(12) United States Patent
Pugh (10) Patent No.: US 8,967,488 B2
(45) Date of Patent: Mar. 3, 2015

(54) OPHTHALMIC LENS WITH COMMUNICATION SYSTEM (71) Applicant: Johnson & Johnson Vision Care, Inc., Jacksonville, FL (US)

(72) Inventor: Randall B. Pugh, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 95 days.

(21) Appl. No.: 13/896,662

(22) Filed: May 17, 2013

(65) Prior Publication Data

US 2014/0340631 A1  Nov. 20, 2014

(51) Int. Cl.
G06K 19/06 (2006.01)
G02C 7/02 (2006.01)

(52) U.S. Cl.
CPC ................................. *G02C 7/022* (2013.01)
USPC .......................................................... 235/494

(58) Field of Classification Search
USPC ........... 351/163, 159, 177; 235/494, 487, 549
See application file for complete search history.

(56) References Cited

U.S. PATENT DOCUMENTS

| 5,257,198 A * | 10/1993 | van Schoyck ................ 700/160 |
| 2009/0244477 A1 | 10/2009 | Pugh et al. |
| 2009/0302122 A1 * | 12/2009 | Begon .......................... 235/494 |
| 2011/0084834 A1 | 4/2011 | Sabeta |

FOREIGN PATENT DOCUMENTS

WO  2008109867 A2  9/2008

OTHER PUBLICATIONS

WO PCT Search Report PCT US2014 038089 Date of Completion Aug. 8, 2014 Date of Mailing Aug. 12, 2014.

* cited by examiner

Primary Examiner — Hung Dang (57) ABSTRACT

An ophthalmic device includes a communication system including an antenna energy receptor and a processor configured to generate a unique identifier. The unique identifier can be, or include, a pedigree profile that can be accessed to prevent users from being exposed to counterfeited ophthalmic devices. The communication system may be small enough to permit incorporation the ophthalmic device without significantly hindering vision, and/or positioned in a media insert with significantly opaque components positioned outside of the optic zone.

20 Claims, 8 Drawing Sheets

OPHTHALMIC LENS WITH COMMUNICATION SYSTEM

TECHNICAL FIELD

The disclosure generally relates to an ophthalmic lens and, more particularly, relates to a hydrogel lens including an antenna communication system.

BACKGROUND

Traditionally, ophthalmic devices, such as a hydrogel lens, an intraocular lens or a punctal plug, include corrective, cosmetic or therapeutic qualities. A contact lens, for example, may provide vision correcting functionality, cosmetic enhancement, and/or therapeutic effects. Each function is provided by a physical characteristic of the contact lens. For example, a refractive quality may provide a vision corrective function, a pigment may provide a cosmetic enhancement, and an active agent may provide a therapeutic functionality.

Ophthalmic lens manufacturing processes include, for example, sandwiching a monomer between back curve (upper) and front curve (lower) mold sections carried in a mold array. The monomer is polymerized, thus forming a lens, which is then removed from the mold sections and further treated in a hydration bath and packaged for consumer use. A more recently developed manufacturing process for manufacturing high quality customized ophthalmic lenses is disclosed in U.S. Pat. No. 7,905,594 to Widman, et al. which is assigned to the assignee of the present disclosure.

In order to reach greater design ranges and higher optical quality, currently, these and other manufacturing techniques are carried out by partially automated and semi-automated apparatus and processes with strict process controls and tight tolerances necessary for the production of high quality ophthalmic lenses. Evolving techniques employ different process controls seeking to improve or add a particular manufacturing step. Examples of newly developed methodologies include new ways of demolding the lens from the mold part, the application of binder layers to the mold parts, polymerization techniques, lens hydration techniques, metrology techniques, lens material development, and the such.

With new methods and lens components being developed, the complexity of troubleshooting the desired automated process controls is sometimes greater. In addition, because some faults may not be detected prior to the detection of a defective ophthalmic lens during quality control, fault identification and correction can often be subject to a time delay wasting production time and materials. As a result, while the aforementioned production processes have some efficacy in the production of soft contact lenses, they suffer a number of disadvantages which can hinder the development of a high speed automated production line capable of producing high quality ophthalmic lenses. Furthermore, with the increasing risk of these high quality ophthalmic lenses being counterfeited, it is desirous for the ophthalmic lens to include a communication system useful to provide information about the ophthalmic lens' production.

Therefore, there is a need for a communication system that can be incorporated in an ophthalmic lens and/or mold part during early stages of manufacturing and which can be useful to generate a unique identifier with correlated production information.

SUMMARY

Accordingly, the foregoing needs are met, to a great extent, by one or more embodiments of the communication system.

In accordance with some embodiments, the communication system includes a nano-antenna incorporated into or onto an ophthalmic device during manufacturing and is coded with a unique identifier.

In accordance with some embodiments, an ophthalmic lens comprises a hydrogel portion, and a communication system. The communication system of said ophthalmic lens can be configured to transmit data associated with a pedigree profile of the ophthalmic lens to an external processor. In some embodiments, a media insert with a battery capable of energizing a communication system of said ophthalmic lens can be included.

According to some aspects of the disclosure, a method of providing an ophthalmic lens is disclosed. The method can include: energizing a communication system forming part of the ophthalmic lens; transmitting data relating to a unique identifier to a processor in communication with the communication system; generating a lens pedigree profile and correlating it to the unique identifier; and recording a signal in the communication system that allows access to a database containing the lens pedigree profile.

Certain implementations of the ophthalmic device and communication system including the antenna configuration have been outlined so that the detailed description below may be better understood. There are, of course, additional implementations that will be described below and which will form the subject matter of the claims.

In this respect, before explaining at least one implementation in detail, it is to be understood that the hydrogel lens including the communication system is not limited in its application to the details of construction and to the arrangements of the components set forth in the following description or illustrated in the drawings. Also, it is to be understood that the phraseology and terminology employed herein, as well as in the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the ophthalmic lens including the control, subsequent to the manufacturing of the ophthalmic lens, of dynamic components that may be included in some embodiments. It is understood, therefore, that the claims include such equivalent constructions insofar as they do not depart from the spirit and scope of the present application.

DETAILED DESCRIPTION

A communication system for an ophthalmic lens is disclosed. The communication system may be used to monitor manufacturing controlled conditions and identify deficiencies in the system in a sensible manner. In some embodiments, the communication system can also be used to generate a Lens Pedigree Profile that can be useful to ensure the correct ophthalmic lens reaches the consumer. For example, the Lens Pedigree Profile can include lens design information useful to verify the authenticity of the ophthalmic lens.

GLOSSARY

In the description and the claims, various terms may be used for which the following definitions will apply:

Active Lens Insert: as used herein, may refer to an electronic or electromechanical insert device with controls based upon logic circuits.

Communication System: as used herein, may refer to a wireless communication device that can be configured to transmit and receive electromagnetic radiation from its components. In some embodiments, the communication system can include a nano-antenna, such as a nano-fractal antenna or a nano-yagi-uda type of antenna architecture, and a nano-scale sensor, processor and nano-transceiver. In some preferred embodiments, the communication system can be of negligible size and be without consequence in most optical plastic polymer or resin applications. In alternative embodiments, significantly opaque components of larger communication systems that would impede vision may be positioned outside of the optical zone, for example, forming part of a Media Insert.

Energized: as used herein, may refer to the state of being able to supply electrical current to or to have electrical energy stored within.

Energy: as used herein, may refer to the capacity of a physical system to do work. Many uses within this disclosure may relate to the said capacity being able to perform electrical actions in doing work.

Energy Receptor: as used herein, may refer to a medium that can functions as an antenna for receiving wireless energy, such as, for example via radio wave transmission.

Energy Source: as used herein, may refer to device or layer which is capable of supplying Energy or placing a logical or electrical device in an Energized state.

Functionalized Layer Insert: as used herein, may refer to an insert for an ophthalmic device formed from multiple functional layers from which at least a portion of the multiple functional layers are stacked. The multiple layers may have unique functionality for each layer; or alternatively mixed functionality in multiple layers. In some embodiments, the layers can be rings.

Lens Design: as used herein, may refer to form, function and/or appearance of a desired Lens, which if fabricated, may provide functional characteristics comprising but not limited to optical power correction, color appearance, therapeutic functionality, wearability, acceptable permeability, shape, composition, conformability, acceptable lens fit (e.g., corneal coverage and movement), and acceptable lens rotation stability.

Lens Forming Mixture: as used herein, the term "lens forming mixture" or "Reactive Mixture" or "RMM" (reactive monomer mixture) refers to a monomer or prepolymer material which can be cured and crosslinked or crosslinked to form an Ophthalmic Lens. Various embodiments can include lens forming mixtures with one or more additives such as: UV blockers, tints, photoinitiators or catalysts, and other additives one might desire in an ophthalmic lenses such as, contact or intraocular lenses.

Lens Forming Surface: as used herein, may refer to a surface that is used to mold at least a portion of a lens. In some embodiments, any such surface, for example 103-104, can have an optical quality surface finish, which indicates that it is sufficiently smooth and formed so that a lens surface fashioned by the polymerization of a lens forming material in contact with the molding surface is optically acceptable. Further, in some embodiments, the lens forming surface can have a geometry that is necessary to impart to the lens surface the desired optical characteristics, including without limitation, spherical, aspherical and cylinder power, wave front aberration correction, corneal topography correction and the like as well as any combinations thereof.

Media Insert: as used herein, may refer to a formable or rigid substrate capable of supporting an energization element, such as a battery, within an ophthalmic lens. In some embodiments, the media insert also includes one or more variable optic lenses and communication systems.

Mold: as used herein, may refer to a rigid or semi-rigid object that may be used to form lenses from uncured formulations. Some molds can include one or more mold parts used to form a hydrogel lens comprising raised portions.

Ocular Surface: as used herein, may refer to the anterior surface area of the eye.

Ophthalmic Lens: as used herein, may refer to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the disclosure are soft contact lenses are made from silicone elastomers or hydrogels, which include but are not limited to silicone hydrogels, and fluorohydrogels.

Optical Zone: as used herein, may refer to an area of an ophthalmic device or lens through which a wearer of the ophthalmic lens sees after the lens is formed.

Peripheral Zone: as used herein, the term "peripheral zone" or "non-optic zone" may refer to an area of an ophthalmic lens outside of the optic zone of the ophthalmic lens, and therefore outside of a portion of the ophthalmic lens through which a lens wearer sees while wearing the ophthalmic lens on, near or in the eye in a normally prescribed fashion.

Pedigree Profile: as used herein, may refer to the background and/or manufacturing history of an ophthalmic lens. In some preferred embodiments, the pedigree profile can include, for example, one or more of: lens corrective specifications, base curve, material(s), encrypted digital identification data, manufacturing facility information, and authentication data.

Released from a Mold: as used herein, may refer to a lens that is either completely separated from the mold, or is only loosely attached so that it can be removed with mild agitation or pushed off with a swab.

Figure 1:
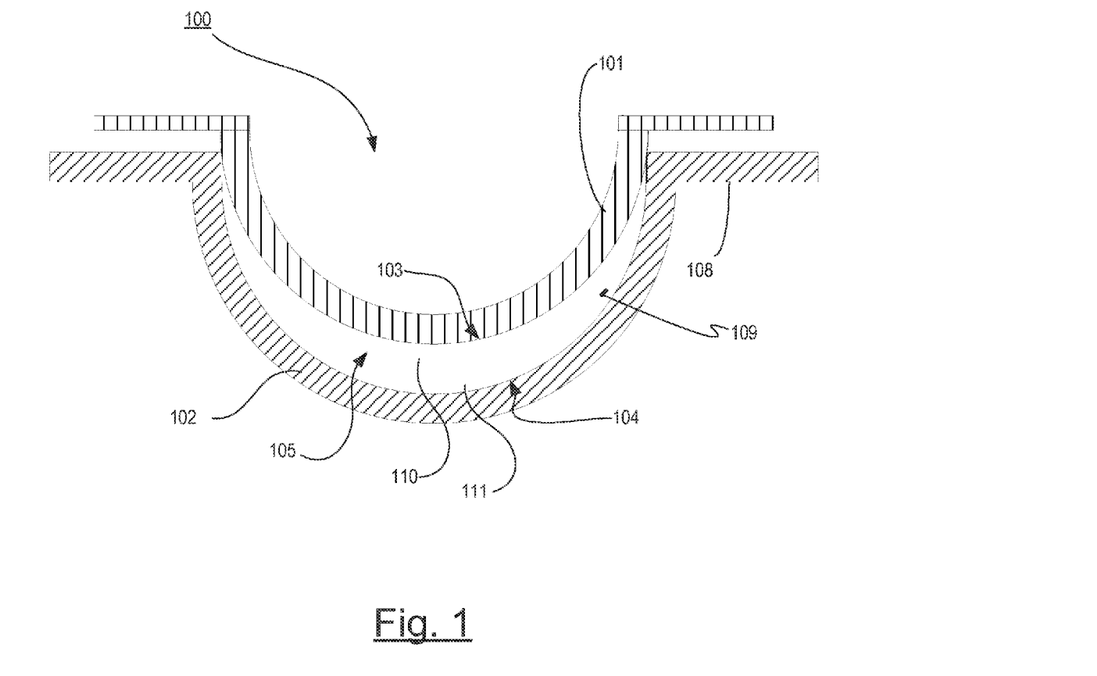
FIG. 1 illustrates a cross section of a mold assembly apparatus according to some embodiments of the disclosure.

Referring now to FIG. 1, a diagram of an exemplary Mold for an Ophthalmic Lens with a Communication System 109 is illustrated. As used herein, the term Mold can include a mold assembly 100 having a cavity 105 into which a Lens forming mixture 110 can be dispensed such that upon reaction or cure of the Lens Forming Mixture, an Ophthalmic Lens of a desired shape is produced. In some embodiments, the Molds and mold assemblies 100 may be made up of more than one "mold parts" or "mold pieces" 101-102. For example, the mold parts 101-102 can be brought together such that a cavity 105 is formed between the mold parts 101-102 in which a lens can be formed. This combination of mold parts 101-102 is preferably temporary. Upon formation of the Ophthalmic Lens, the mold parts 101-102 can again be separated and the Ophthalmic Lens can be Released from a Mold.

At least one mold part 101-102 has at least a portion of its Lens Forming Surface 103-104 in contact with the Lens Forming Mixture such that upon reaction or cure of the Lens Forming Mixture 110 that surface 103-104 provides a desired shape and form to the portion of the Ophthalmic Lens with which it is in contact. The same may be true of at least one other mold part 101-102.

Thus, for example, in one preferred embodiment a mold assembly 100 can be formed from two parts 101-102, a female concave piece (front piece) 102 and a male convex piece (back piece) 101 with a cavity formed between them. The portion of the concave surface 104 which can make contact with Lens Forming Mixture 110 has the curvature of the front curve of an Ophthalmic Lens to be produced in the mold assembly 100 and is sufficiently smooth and formed such that the surface of an Ophthalmic Lens formed by polymerization of the Lens Forming Mixture which is in contact with the concave surface 104 is optically acceptable.

In some embodiments, the front mold piece 102 can also have an annular flange integral with and surrounding circular circumferential edge 108 and extends from it in a plane normal to the axis and extending from the flange (not shown).

A Lens Forming Surface can include a surface 103-104 with an optical quality surface finish, which indicates that it is sufficiently smooth and formed so that an Ophthalmic Lens surface fashioned by the polymerization of a Lens Forming Mixture in contact with the molding surface is optically acceptable. Further, in some embodiments, the Lens Forming Surface 103-104 can have a geometry that may be necessary to impart to the lens surface the desired optical characteristics, including without limitation, spherical, aspherical and cylinder power, wave front aberration correction, corneal topography correction and the like as well as any combinations thereof.

Mold part 101-102 material can include a polyolefin of one or more of: polypropylene, polystyrene, polyethylene, polymethyl methacrylate, and modified polyolefins. A preferred alicyclic co-polymer contains two different alicyclic polymers and is sold by Zeon Chemicals L.P. under the trade name ZEONOR. There are several different grades of ZEONOR. Various grades may have glass transition temperatures ranging from 105° C. to 160° C. A specifically preferred material is ZEONOR 1060R. Other Mold materials that may be combined with one or more additives to form an Ophthalmic Lens Mold include, for example, Zieglar-Natta polypropylene resins (sometimes referred to as znPP). On exemplary Zieglar-Natta polypropylene resin is available under the name PP 9544 MED. PP 9544 MED is a clarified random copolymer for clean molding as per FDA regulation 21 CFR (c)3.2 made available by ExxonMobile Chemical Company. PP 9544 MED is a random copolymer (znPP) with ethylene group (hereinafter 9544 MED). Other exemplary Zieglar-Natta polypropylene resins include: Atofina Polypropylene 3761 and Atofina Polypropylene 3620WZ. Still further, in some embodiments, the Molds of the disclosure may contain polymers such as polypropylene, polyethylene, polystyrene, polymethyl methacrylate, modified polyolefins containing an ali-cyclic moiety in the main chain and cyclic polyolefins. This blend can be used on either or more Mold parts, for example, where it is preferred that this blend is used on the back curve and the front curve consists of the alicyclic co-polymers.

In some preferred methods of making Molds 100, injection molding can be utilized according to known techniques, however, embodiments can also include Molds fashioned by other techniques including, for example: lathing, diamond turning, or laser cutting. Typically, lenses are formed on at least one surface of both Mold parts 101-102. However, in some embodiments, one surface of an Ophthalmic Lens may be formed from a Mold part 101-102 and another surface of a lens can be free-formed as described by other methods.

Lenses

Figure 2:
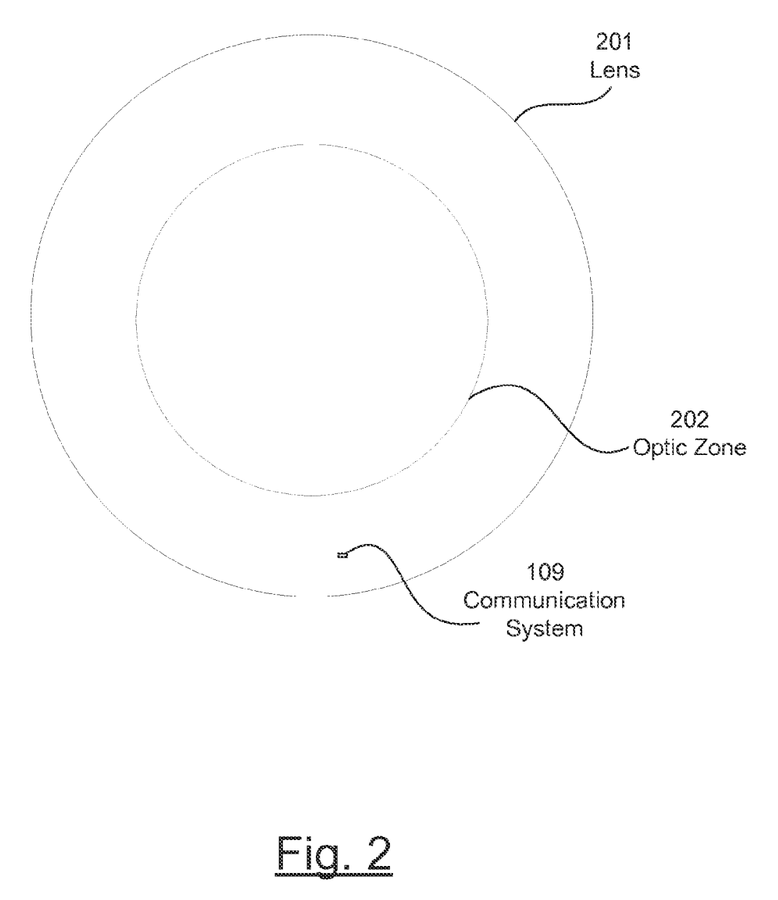
FIG. 2 illustrates an ophthalmic lens with a communication system including an energy receptor according to some embodiments of the disclosure.
Figure 4:
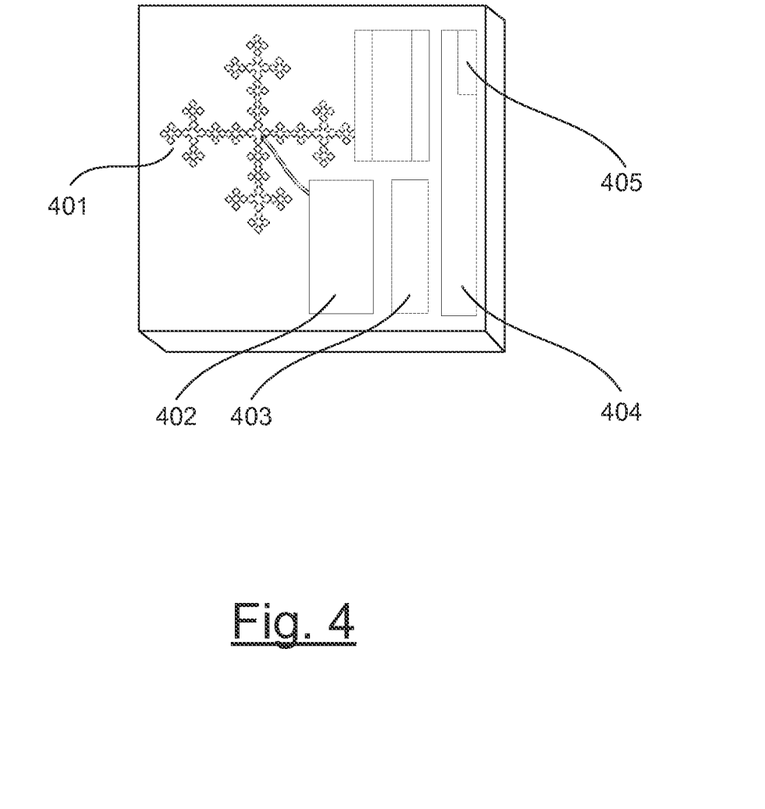
FIG. 4 illustrates a schematic design of a communication system comprising an exemplary nano-antenna according to some aspects of the disclosure.

Referring now to FIG. 2, an exemplary Ophthalmic Lens 201 is illustrated with a Communication System 109, including a nano-antenna 401 (shown in FIG. 4) and a nano-processing device 404 (shown in FIG. 4). As shown in FIG. 4, the nano-antenna 401 can be an Energy Receptor and may be a fractal nano-antenna of a conductive material, such as, a metallic material. Suitable metallic materials can include, for example, gold, grapheme, silver and copper. Conductive fibers such as conductive carbon fibers can also be suitable.

The nano-antenna 401 can be in electrical communication with a processing device 404. The processing device 404 can include any semiconductor type chip. In some specific embodiments, the processing device includes one or more nan-sensor(s) 406 (shown in FIG. 4). The processing device 404 may also include multiple devices or circuitry. In an effort to provide simplicity in this description, the one or more devices will generally be referred to in the singular.

Referring back to FIG. 2, as illustrated, the Communication System 109 can be located outside of an Optical Zone 202, wherein the Optical Zone 202 includes that portion of the Ophthalmic Lens 201 providing line of sight for a wearer of the Ophthalmic Lens 201. In some embodiments, the Communication System 109 may be small enough to not have a significant optical effect when it is placed in the Optical Zone 202 and its location may not be constrained to the Peripheral Zone.

A preferred Ophthalmic Lens type can include a Ophthalmic Lens 201 that includes a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups. Suitable silicone containing components include compounds of:

Formula I where $R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof; where b=0 to 500, where it is understood that when b is other than 0, b is a distribution having a mode equal to a stated value; wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$ alkenylphenyl $C_{1-6}$ alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof. Suitable monovalent alkyl and aryl groups include unsubstituted monovalent $C_1$ to $C_{1-6}$ alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one embodiment b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris (trimethylsiloxy) silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS"). In another embodiment b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In one embodiment, where a silicone hydrogel lens is desired, the lens of the present disclosure will be made from a reactive mixture comprising at least about 20 and preferably between about 20 and 70% wt silicone containing components based on total weight of reactive monomer components from which the polymer is made. In another embodiment, one to four $R^1$ comprises a vinyl carbonate or carbamate of the formula:

Formula II wherein: Y denotes O—, S— or NH—; R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris (trimethylsiloxy)silane]; 3-[tris (trimethylsiloxy)silyl] propyl allyl carbamate; 3-[tris (trimethylsiloxy)silyl] propyl vinyl carbamate; trimethylsilylethyl vinyl carbonate; trimethylsilylmethyl vinyl carbonate, and where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

Formula IV-VI wherein: D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain; * denotes a urethane or ureido linkage; $_a$ is at least 1; A denotes a divalent polymeric radical of formula:

Formula VII

$R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1. A preferred silicone-containing component is a polyurethane macromer represented by the following formula:

Formula IX wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

ysiloxanes with a polar fluorinated graft or side group having a hydrogen atom attached to a terminal difluoro-substituted carbon atom; hydrophilic siloxanyl methacrylates containing ether and siloxanyl linkages and crosslinkable monomers containing polyether and polysiloxanyl groups. Any of the foregoing polysiloxanes can also be used as the silicone containing component in this disclosure.

Figure 3:
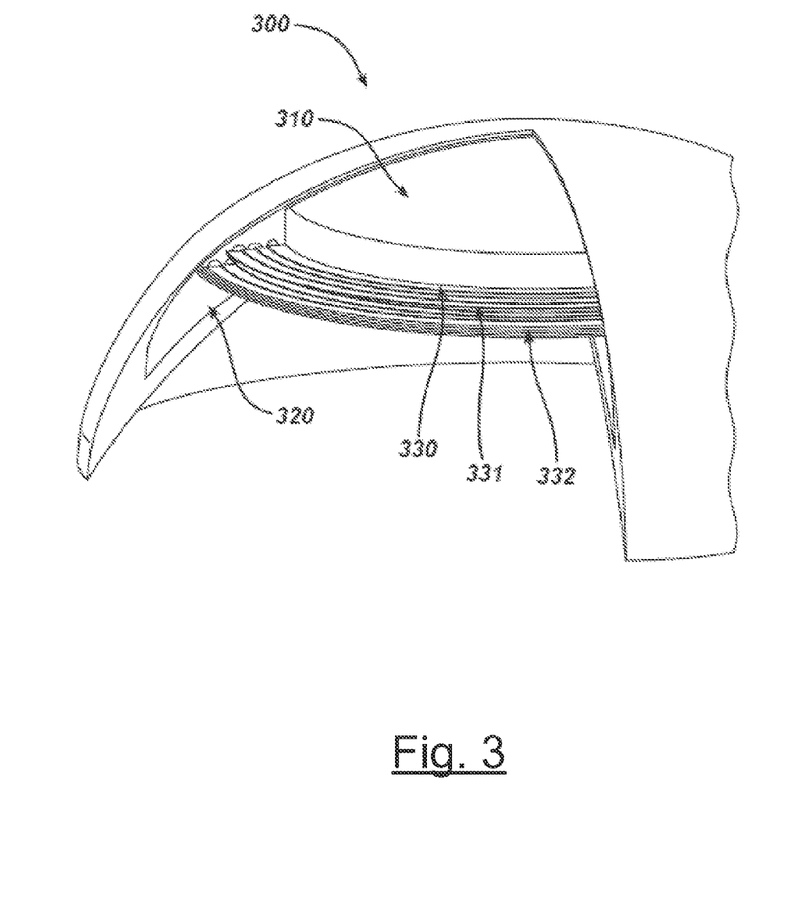
FIG. 3 illustrates another ophthalmic lens with a media insert comprising a communication system according to some embodiments of the disclosure.

Referring now to FIG. 3 a three dimensional cross section representation is illustrated of an exemplary Ophthalmic Lens 300 including a Functionalized Layer Media Insert 320 configured to include Communication System components on one or more of its layers 330, 331, 332. In the present exemplary embodiment, the Media Insert 320 surrounds the entire periphery of the Ophthalmic Lens 300. One skilled in the art can understand that the actual Media Insert 320 may comprise a full annular ring or other shapes that still may reside inside or on the hydrogel portion of the Ophthalmic lens 300 and be within the size and geometry constraints presented by the ophthalmic environment of the user.

Layers 330, 331 and 332 are meant to illustrate three of numerous layers that may be found in a Media Insert 320 formed as a stack of functional layers. In some embodiments, for example, a single layer may include one or more of: active and passive components and portions with structural, electrical or physical properties conducive to a particular purpose including the Communication System functions described in the present disclosure. Furthermore, in some embodiments, a layer 330 may include an Energy Source, such as, one or more of: a battery, a capacitor and a receiver within the layer 330. Item 331 then, in a non-limiting exemplary sense may comprise microcircuitry in a layer that detects actuation signals for the Ophthalmic Lens 300. In some embodiments, a power regulation layer 332, may be included that is capable of receiving power from external sources, charges the battery layer 330 and controls the use of battery power from layer 330 when the Ophthalmic Lens 300 is not in a charging environment. The power regulation may also control signals to an exemplary active lens, demonstrated as item 310 in the center annular cutout of the Media Insert 320.

Other silicone containing components suitable for use in this disclosure include macromers containing polysiloxane, polyalkylene ether, diisocyanate, polyfluorinated hydrocarbon, polyfluorinated ether and polysaccharide groups; pol- An energized lens with an embedded Media Insert 320 may include an energy source, such as an electrochemical cell or battery as the storage means for the energy and in some embodiments, encapsulation, and isolation of the materials comprising the energy source from an environment into which an Ophthalmic Lens is placed. In some embodiments, a Media Insert 320 can also include a pattern of circuitry, components, and energy sources. Various embodiments may include the Media Insert 320 locating the pattern of circuitry, components and Energy Sources around a periphery of an Optic Zone through which a wearer of an Ophthalmic Lens would see, while other embodiments may include a pattern of circuitry, components and Energy Sources which are small enough to not adversely affect the sight of the Ophthalmic Lens wearer and therefore the Media Insert 320 may locate them within, or exterior to, an Optical Zone.

Referring now to FIG. 4, a schematic design of the exemplary Communication System 109 of FIG. 1 comprising a nano-antenna 401 according to some aspects of the disclosure is illustrated. In some preferred embodiments, the nano-antenna 401 can be a fractal antenna configured to operate at different frequencies. The nano-antenna 401 may be made up of a conductive material, such as, a metallic material. Suitable metallic materials can include, for example, gold, grapheme, silver and copper. Conductive fibers such as conductive carbon fibers can also be suitable. The nano-antenna may function as an energy receptor configured to provide a self-powered nano-Communication System 109, for example, when it is exposed to a heavy radial frequency field absorbing enough energy to power other electronic components. A fractal shape may include a repeating pattern or any other mathematical set that has a dimension that usually exceeds its topological dimension. Another type of nano-antenna 401 can include a nano-optical Yagi-Uda antenna or the such.

In some embodiments, the nano-antenna 401 can be in communication nano-transceiver 402 which may be configured to perform functions including baseband processing, frequency conversion, filtering and power amplification, of the received signals transmitted into and/or out of the nano-antenna 401. A nano-actuator 403 may also be included in the Communication System 109 to allow one or more nano-sensor(s) 406 to interact with the surrounding environment. Nano-sensors can include, for example, one or more of: physical nano-sensors capable of measuring mass, pressure, force, and/or displacement; chemical nano-sensors configured to measure chemical compositions and/or concentrations; and, biological nan-sensors configured to measure antibody/antigen interaction, DNA interaction, and/or enzymatic interactions. Nano-actuator 403 may include one or more of: physical, chemical or biological actuators. A nano-processing device 404 comprising nano-memory 405 in communication with the sensor 406 can function, for example, to control the recording measured conditions by the sensor 406, execute operational sequences, generate and/or transmit data related to the Ophthalmic Lens Pedigree Profile.

In general, according to the embodiments previously described, a Media Insert 320 and/or self-powered nano-Communication System 109 can be embodied within or on an ophthalmic lens via automation which can places/deposit the components on a desired location relative to a mold part used to fashion the Ophthalmic Lens.

Apparatus

Figure 5:
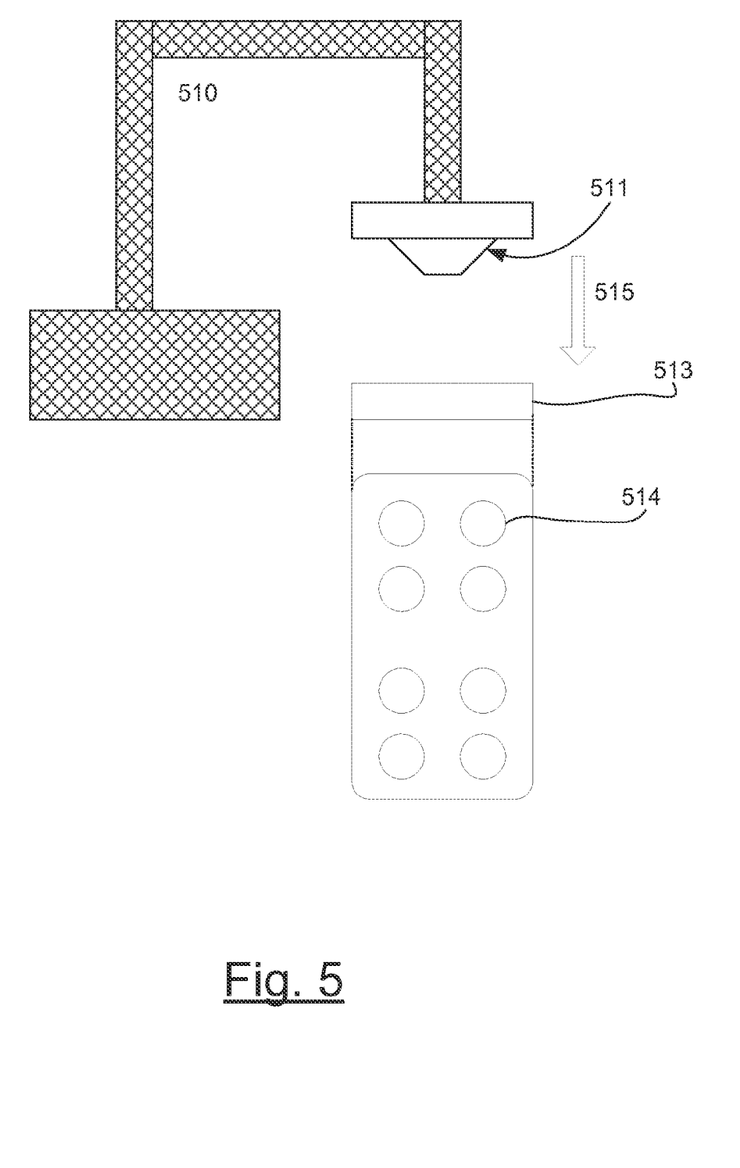
FIG. 5 illustrates an ophthalmic lens manufacturing apparatus that may be used to position a communication system in a mold part for an ophthalmic lens.

Referring now to FIG. 5, automated apparatus 510 is illustrated with one or transfer interfaces 511. As illustrated, multiple mold parts can each be associated with a mold part receptacle 514 contained within a pallet 513 and presented to the transfer interface(s) 511. The transfer interface(s) 511 can place or deposit a standalone Communication System (shown in FIG. 4) or a Media Insert (shown in FIG. 3) containing the Communication System configured to generate an Ophthalmic Lens Pedigree Profile. Embodiments can include, for example, a single interface individually placing a single Communication System on a programmed manner onto a mold part receptacle 514, or multiple interfaces (not shown) simultaneously placing multiple Communication Systems within multiple mold parts, and in some embodiments, within each mold part.

Another aspect of some embodiments includes apparatus to support the Communication System while the hydrogel body of the Ophthalmic Lens is molded around the Communication System. For example, in some embodiments the communication system may affix to holding points in a Mold (not illustrated). In some embodiments, the holding points may preferably be affixed with polymerized material of the same type that will be formed into the lens body.

Figure 6:
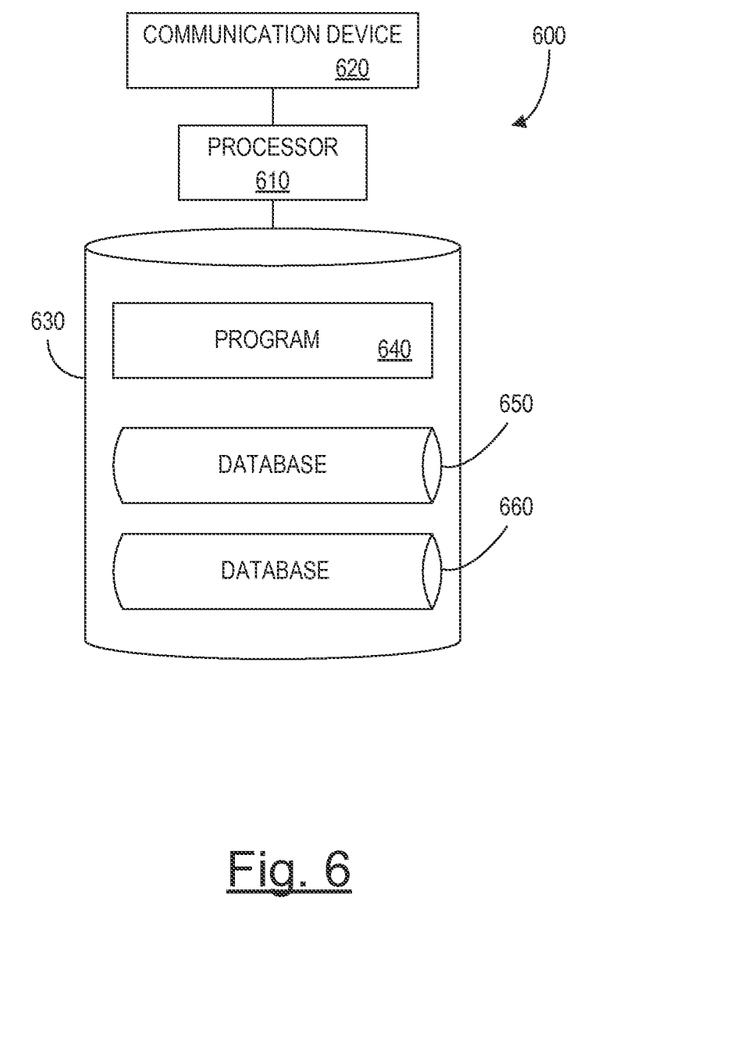
FIG. 6 illustrates a processor that may be used to implement some embodiments of the disclosure.

Referring now to FIG. 6, a schematic diagram of a controller 600 that may be used with some embodiments of the present disclosure is illustrated. The controller 600 includes a processor 610, which may include one or more processor components coupled to a communication device 620. In some embodiments, a controller 600 can be used to transmit energy to the energy source placed in the Ophthalmic Lens.

The controller 600 can include one or more processors 610, coupled to a communication device 620 configured to communicate logical signals via a communication channel. The communication device 620 may be used to electronically control one or more of: the placement of a microcontroller and a flexible media into the Ophthalmic Lens and the transfer of command to operate a component or the microcontroller.

The communication device 620 may also be used to communicate, for example, with one or more controller apparatus or manufacturing equipment components.

The processor 610 is also in communication with a storage device 630. The storage device 630 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 630 can store a program 640 for controlling the processor 610. The processor 610 performs instructions of the program 640, and thereby operates in accordance with the present disclosure. For example, the processor 610 may transmit data including, for example, unique identifier, sensor data, design information and other data that can be included in the Pedigree Profile. The storage device 630 can also store ophthalmic related data in one or more databases 650-660. The database may include customized user data, Ophthalmic Lens Pedigree profiles, metrology data, and specific control sequences for controlling energy to and from the Communication System.

In some embodiments, an Ophthalmic Lens with an activation component operative to provide energy from an energy source incorporated into a Media Insert.

Figure 7:
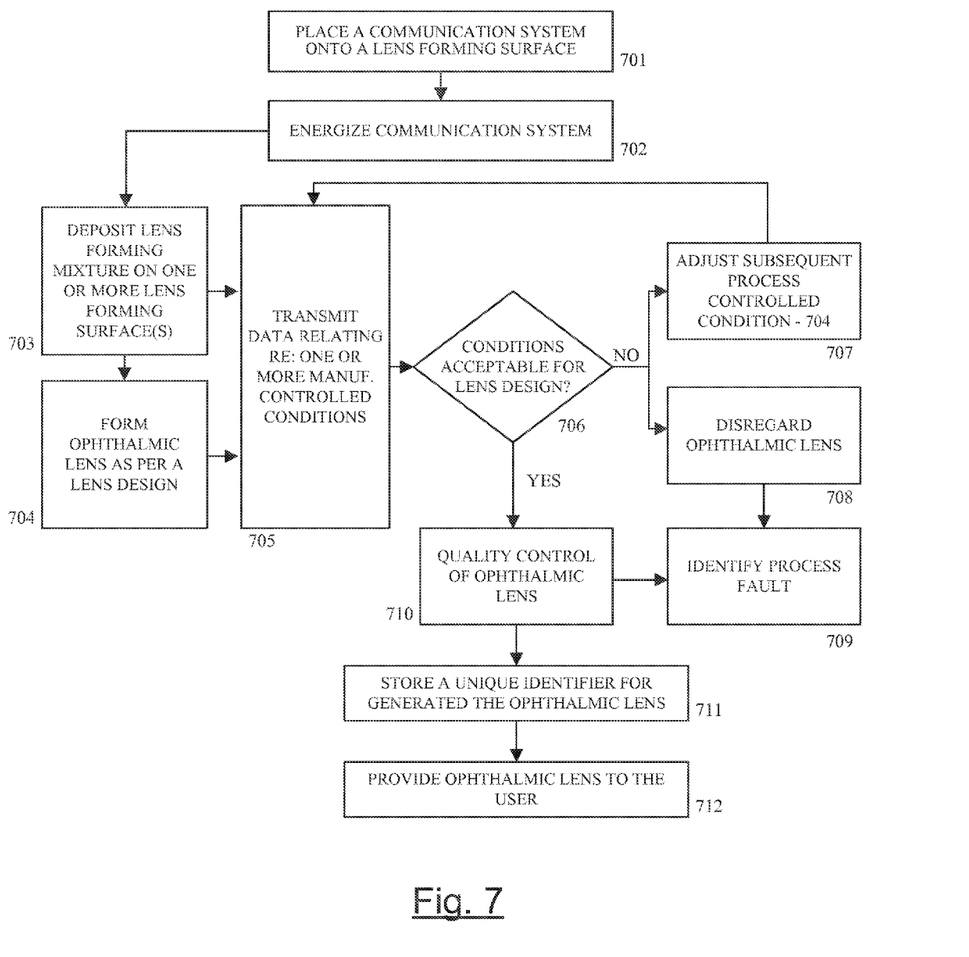
FIG. 7 illustrates method steps that may be used to generate an ophthalmic lens pedigree profile during manufacturing.

Referring now to FIG. 7, method steps that can be used to generate an Ophthalmic Lens Pedigree Profile are shown. At 701, a Communication System is energized. Energization may take place, for example, using an internal Energy Source contained in a Media Insert and/or through a nano-antenna configured to be an energy receptor and energize other components of the Communication System when it is placed in a high frequency field.

At 705, data relating to a unique identifier can be transmitted to a database included in one or both of a database stored in memory contained within the Communication System and a database of an external processor in communication with the Communication System. The unique identifier may be a serial number that can be recorded during the manufacturing of the die and/or a numerical value assigned to a Pedigree Profile generated throughout the manufacturing of the Ophthalmic Lens 710. In some preferred embodiments, the unique identifier may be stored in a database and correlated to additional information. Additional information can include, for example, lens manufacturer information, customer/user data, lens design, Pedigree Profile and the like. Further, in some embodiments, the unique identifier can be encrypted and recorded in a coded signal that can be used to access said Pedigree Profile. The coded signal can be recorded in the Communication System and accessed by an external system, for example, on demand to protect the user by ensuring the Ophthalmic Lens is not a counterfeited product. In addition to ensuring authenticity, additional information relating to the Ophthalmic Lens, patient, and/or manufacturer that may be stored in a database and associated with the Ophthalmic Lens may be accessed.

Figure 8:
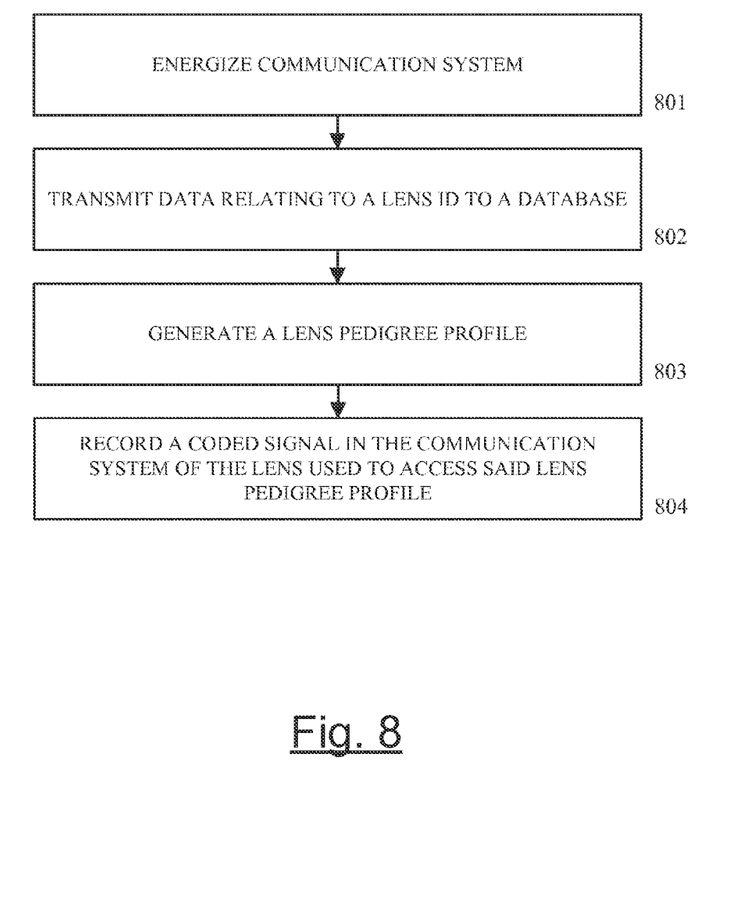
FIG. 8 illustrates method steps that may be used to monitor and/or troubleshoot manufacturing controlled conditions.

Referring now to FIG. 8, exemplary method steps that may be used to monitor and/or troubleshoot manufacturing controlled conditions are shown. At 801, a Communication System is placed on a Lens Forming Surface. At 805, the Communication System can be energized. At 810, a Lens Forming Mixture is put in contact with the Lens Forming Surface by immersion of the Lens Forming Mixture onto a container or depositing the Lens Forming Mixture to the Mold including the Lens Forming Surface. At 815, the Ophthalmic Lens can be formed according to an Ophthalmic Lens design using a suitable manufacturing method. Controlled conditions or processed during the depositing of the Lens Forming Mixture 810 and/or the forming of the Ophthalmic Lens 815 can be monitored using one or more sensors in communication with, and/or comprised by, the Communication System. At 820, data relating to a controlled condition can be transmitted to a processor. At 825, the processor can compare predetermined thresholds values to the transmitted data to conform to the Ophthalmic Lens design. At 830, when the measured data is determined to be outside the predetermined threshold, the processor may modify a subsequent process controlled condition to counteract the previous deficiency if appropriate. At 835, the processor may categorize the Ophthalmic Lens as a non-conforming one that should be discarded.

At 840, the Ophthalmic Lens may undergo quality control procedures in which controlled conditions may also be monitored. When a non-conformity/fault is identified, either during the manufacturing 835 or the quality control process 840, the recorded data may be used to identify the accounted process fault for the non-conformity in the manufacturing line 845. In some preferred embodiments, the processor may additionally send an alert to the manufacturing line operator/controller and stop the line until further input is provided by the operator/controller. As previously mentioned, all of the transmitted data may be recorded in a database and used to generate the Pedigree Profile corresponding to the unique identifier stored in the Communication System 850.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

What is claimed is:

1. An ophthalmic lens comprising:
a hydrogel portion, and
a communication system of said ophthalmic lens configured to transmit data associated with a pedigree profile of the ophthalmic lens to an external processor.

2. The ophthalmic lens of claim 1, wherein:
the communication system of said ophthalmic lens comprises a fractal nano-antenna configured to be an energy receptor and energize the communication system.

3. The ophthalmic lens of claim 1, wherein:
the communication system of said ophthalmic lens comprises a Yagi-Uda nano-antenna configured to be an energy receptor and energize the communication system.

4. The ophthalmic lens of claim 1, additionally comprising:
a unique identifier stored in the communication system of said ophthalmic lens.

5. The ophthalmic lens of claim 4, wherein:
the communication system of said ophthalmic lens comprises one or more nano-sensor(s) capable of providing sensor data corresponding to one or more manufacturing controlled condition(s).

6. The ophthalmic lens of claim 5, wherein:
at least a portion of the sensor data forms part of the unique identifier.

7. The ophthalmic lens of claim 6, wherein:
the unique identifier is encrypted to prevent unwanted replication.

8. The ophthalmic lens of claim 1, additionally comprising:
an encapsulant around the communication system of said ophthalmic lens.

9. The ophthalmic lens of claim 1, wherein:
the hydrogel portion of the ophthalmic lens includes a 20-70 percent silicon hydrogel composition.

10. The ophthalmic lens of claim 1, wherein:
the communication system of said ophthalmic lens is included in the optic zone of the ophthalmic lens.

11. An ophthalmic lens comprising:
a hydrogel portion, and
a media insert comprising a battery capable of energizing a communication system of said ophthalmic lens configured to transmit data associated with a pedigree profile of the ophthalmic lens to an external processor.

12. The ophthalmic lens of claim 11, wherein:
a unique identifier stored in the communication system of said ophthalmic lens.

13. The ophthalmic lens of claim 12, comprising:
one or more sensor(s) capable of providing sensor data corresponding to one or more manufacturing controlled condition(s).

14. The ophthalmic lens of claim 13, wherein:
at least a portion of the sensor data forms part of the unique identifier.

15. The ophthalmic lens of claim 14, wherein:
the unique identifier is encrypted to prevent unwanted replication.

16. The ophthalmic lens of claim 11, wherein:
the hydrogel portion of the ophthalmic lens includes a 20-70 percent silicon hydrogel composition.

17. The ophthalmic lens of claim 11, wherein:
significantly opaque components of the communication system of said ophthalmic lens are supported by at least a portion of the media insert outside of the optic zone of the ophthalmic lens.

18. A method of providing an ophthalmic lens pedigree profile comprising:
energizing a communication system forming part of the ophthalmic lens;
transmitting data relating to a unique identifier to a processor in communication with the communication system;
generating a lens pedigree profile and correlating it to the unique identifier; and recording a signal in the communication system that allows access to a database containing the lens pedigree profile.

19. The method of claim 18, wherein:

the recorded signal is encrypted to prevent unwanted replication.

20. The method of claim 18, wherein:

the pedigree profile includes one or both lens design information and manufacturing controlled process condition(s) information.

* * * * *